(12) United States Patent
Morfill et al.

(10) Patent No.: US 7,683,342 B2
(45) Date of Patent: Mar. 23, 2010

(54) PLASMA SOURCE

(75) Inventors: Gregor Morfill, Munich (DE); Tetsuji Shimizu, Garching (DE); Bernd Steffes, Garching (DE); Shuitsu Fujii, Fukuyama (JP)

(73) Assignees: Max-Planck Gesellschaft zur Forderung der Wissenschaften e. V. (DE); Adtec Europe Limited (GB)

( * ) Notice: Subject to any disclaimer, the term of this patent is extended or adjusted under 35 U.S.C. 154(b) by 58 days.

(21) Appl. No.: 12/065,230

(22) PCT Filed: Sep. 11, 2006

(86) PCT No.: PCT/EP2006/008824

§ 371 (c)(1),
(2), (4) Date: Apr. 9, 2008

(87) PCT Pub. No.: WO2007/031250

PCT Pub. Date: Mar. 22, 2007

(65) Prior Publication Data

US 2008/0237484 A1    Oct. 2, 2008

(30) Foreign Application Priority Data

Sep. 16, 2005   (EP) .................................. 05108538

(51) Int. Cl.
*H05H 1/46* (2006.01)
*B23K 9/02* (2006.01)
*H01J 27/00* (2006.01)
*A61B 18/04* (2006.01)

(52) U.S. Cl. ............... 250/427; 250/423 R; 333/99 PL; 219/121.48; 219/121.5; 219/121.52

(58) Field of Classification Search ................. 250/427, 250/423 R; 333/99 R, 99 PL; 219/121.36, 219/121.43, 121.47, 121.48, 121.54, 121.57, 219/121.59, 121.5, 121.51, 121.52, 121.55
See application file for complete search history.

(56) References Cited

U.S. PATENT DOCUMENTS 3,075,065 A * 1/1963 Buhler et al. .................. 219/75
4,731,517 A * 3/1988 Cheney .................. 219/121.59
5,247,152 A * 9/1993 Blankenship .......... 219/121.49

(Continued)

FOREIGN PATENT DOCUMENTS

WO    WO 2007/031250 A1    3/2007

OTHER PUBLICATIONS

Stoffels E. et al: "Plasma Needle: A Non-Destructive Atmospheric Plasma Source for Fine Surface Treatment of (Bio) Materials," Plasma Sources, Science and Technology Iop Publishing UK, vol. 11, No. 4, Nov. 2002, pp. 383-388, XP002368047 ISSN: 0963-0252.

*Primary Examiner*—Bernard E Souw
(74) *Attorney, Agent, or Firm*—DLA Piper LLP (US)

(57) ABSTRACT

A plasma source, particularly for disinfection of wounds, comprising: an ionization chamber having an inlet for introducing a gas into the ionization chamber and further having an outlet for dispensing the ionized gas onto an object; several ionization electrodes being disposed within the ionization chamber for ionizing the gas and a predetermined ratio of the electrode-electrode distance on the one hand and the electrode-wall distance on the other hand, wherein the ratio is in a range approximately between about 1.8 and about 2.2.

18 Claims, 8 Drawing Sheets

U.S. PATENT DOCUMENTS

| | | |
|---|---|---|
| 5,332,885 A | 7/1994 | Landes |
| 5,532,448 A * | 7/1996 | Schlienger ............ 219/121.43 |
| 5,825,485 A * | 10/1998 | Cohn et al. ................. 356/316 |
| 5,965,039 A * | 10/1999 | Kitahashi et al. ......... 219/121.5 |
| 6,081,329 A * | 6/2000 | Cohn et al. ................. 356/316 |
| 6,355,904 B1 * | 3/2002 | Batdorf et al. ......... 219/121.59 |
| 6,429,935 B1 * | 8/2002 | Duan ........................ 356/316 |
| 6,552,295 B2 * | 4/2003 | Markunas et al. ...... 219/121.36 |
| 2002/0040889 A1 * | 4/2002 | Markunas et al. ...... 219/121.36 |
| 2004/0138527 A1 | 7/2004 | Bonner et al. |
| 2006/0237399 A1 * | 10/2006 | Horner-Richardson et al. .................... 219/121.51 |
| 2007/0017636 A1 * | 1/2007 | Goto et al. ............. 156/345.47 |
| 2008/0210669 A1 * | 9/2008 | Yang et al. ............. 219/121.49 |
| 2008/0237484 A1 * | 10/2008 | Morfill et al. ............... 250/427 |

\* cited by examiner

PLASMA SOURCE

RELATED APPLICATION

This is a §371 of International Application No. PCT/EP2006/008824, with an international filing date of Sep. 11, 2006 (WO 2007/031250 A1, published Mar. 22, 2007), which is based on European Patent Application No. 05108538.9 filed Sep. 16, 2005.

TECHNICAL FIELD

The invention relates to a plasma source, particularly for disinfection of wounds.

BACKGROUND

The use of non-equilibrium plasmas for the in vivo sterilization of wounds has been discussed in Stoffels, E.; Stoffels, W.: "The healing touch of a micro-plasma", published on http://www.phys.tue.nl. However, the in vivo sterilization of wounds requires low temperatures of the plasma and a low electromagnetic irradiation, so that the conventional plasma sources are not suitable for the in vivo sterilization of wounds.

Further, U.S. Pat. No. 5,332,885 discloses a plasma spray apparatus for spraying powdery or gaseous material onto a substrate surface, e.g. for coating the substrate. However, due to the high temperature of the plasma output, this plasma spray apparatus is not suitable for the in vivo sterilisation of wounds.

A so-called plasma needle is disclosed in Stoffels, E. et al.: "Plasma needle: a non-destructive atmospheric plasma source for fine surface treatment of (bio)materials", Plasma Source Sci. Technol. 11 (2002) 383-388. This plasma needle comprises a single electrode being disposed within a grounded metal cylinder with 1 cm inner diameter. However, the aforementioned plasma needle is not suitable for a large-area sterilisation of wounds since the outlet of the metal cylinder is very small.

Moreover, US 2004/0138527 A1 discloses a tubular suction tool for accessing an anatomic surface or anatomic space and particularly the pericardium to access pericardial space and the epicardial surface of the heart to implant cardiac leads in a minimally invasive manner are disclosed. Therefore, this reference is not pertinent to the present application.

SUMMARY

It is therefore an aspect of an exemplary embodiment the invention to improve the afore-mentioned plasma source.

As an example, an embodiment provides a plasma source, which is suitable for the large-area in vivo sterilization of wounds.

According to an illustrative example, a plasma source is provided comprising an ionization chamber having an inlet for introducing a gas into the ionization chamber and further having an outlet for dispensing the ionized gas onto an object, e.g. a wound of a patient. Further, the plasma source comprises several ionization electrodes being disposed within the ionization chamber for ionizing the gas. In the plasma source there is a specified distance between adjacent ionization electrodes and also a specified distance between each ionization electrode and the inner wall of the ionization chamber. Further, the plasma source is characterized by a specified ratio of the electrode-electrode distance on the one hand and the electrode-wall distance on the other end, wherein the ratio is in a range between 1.8 and 2.2. In one embodiment, the ratio of the electrode-electrode distance on the one hand and the electrode-wall distance on the other hand is substantially 2, i.e. the electrode-electrode distance is two times bigger than the electrode-wall distance.

This ratio advantageously results in both an easy discharge trigger and a steady operation of all ionization electrodes. Therefore, the plasma source provides a large plasma output with a low energy input, so that the plasma source is well suitable for in vivo applications, e.g. sterilization of wounds, treatment of bacteriological, fungicidal and viral skin disorders, since it combines a comparatively low temperature of the plasma with a low electromagnetic irradiation.

It should be noted that the afore-mentioned values for the ratio between the electrode-electrode distance on the one hand and the electrode-wall distance on the other end may refer to the end o the ionization electrodes, where the plasma is actually generated. For example, the inner diameter of the ionization chamber might vary along the ionization electrodes, so that the aforementioned ratio accordingly varies even in case of a constant electrode-electrode distance. In such a case, a ratio is defined between the electrode-electrode distance and the electrode-wall distance at the end of the ionization electrodes.

However, it is possible that the ratio between the electrode-electrode distance and the electrode-wall distance is within the specified range (e.g. 1.8-2.2) over the entire length of the ionization electrodes and not only at the end of the ionization electrodes.

In an exemplary embodiment of the invention, the plasma source comprises six ionization electrodes. Experiments using argon for the generation of the plasma have shown that the conversion efficiency (plasma output per electrode) increases with the number of ionization electrodes approximately linearly up to a number of six ionization electrodes. Then, the efficiency flattens out and eventually decreases. Therefore, a plasma torch with six ionization electrodes is the optimum for argon gas. However, the invention is not restricted to plasma sources having six electrodes. For example, it is also possible to provide 3, 4, 5, 7, 8, 9, 10, 11 or 12 ionization electrodes within the ionization chamber.

Further, the ionization electrodes may be rod-shaped and arranged parallel to each other forming an equilateral polygon in cross-section. In such an embodiment the distance between adjacent ionization electrodes, i.e. the electrode-electrode distance, is uniform within the electrode arrangement. However, the invention is not restricted to electrode arrangements having a uniform electrode-electrode distance. Instead, the electrode-electrode distance might vary within the electrode arrangement from electrode to electrode. Further, the distance between the ionization electrodes and the inner wall of the ionization chamber may be uniform within the entire electrode arrangement. However, the invention is not restricted to such embodiments having a uniform electrode-wall distance. Instead, the electrode-wall distance might vary within the electrode arrangement from electrode to electrode.

Further, the ionization electrodes may have an at least partially serrated surface, which can be realized by using screws having an external thread as the ionization electrodes. In this manner, an easy discharge trigger and a steady operation of the ionization electrodes is facilitated.

The ionization electrodes may be made from aluminium. An advantage of aluminium is that it does not develop a polymerized coating, which might "flake off". Further, ionization electrodes consisting of aluminium have a better plasma efficiency.

However, it is also possible to use ionization electrodes made from stainless steel. An advantage of lionization electrodes consisting of stainless steel is that they are particularly suitable for sterilisation purposes.

The ionization electrodes may ionize the gas within the ionization chamber by emitting microwaves. Therefore, the plasma source may comprises an electrical terminal for externally connecting the ionization electrodes to a micro wave generator. However, the invention is not restricted to plasma sources in which the plasma is generated by microwaves. Instead, it is possible to use radio frequency (R.F.) or even direct current for ionizing the gas within the ionization chamber.

However, if the plasma is generated by microwaves, the length of the ionization electrodes may be matched to the wavelength of the microwaves. For example, the length l of the ionization electrodes might correspond to the wavelength $\lambda$ of the microwaves. Alternatively, the length l of the ionization electrodes might correspond to half the wavelength $\lambda/2$.

In an exemplary embodiment of the plasma source the walls of the ionization chamber are made from an electrically conductive material, e.g. aluminium, so that the walls of the ionization chamber are shielding the microwaves emitted by the ionization electrodes. In this manner, the electromagnetic radiation leaving the ionization chamber is reduced, which allows in vivo plasma applications.

Further, the outlet of the ionization chamber may be covered by a mesh to avoid an unwanted accidental contact with the ionization electrodes.

Further, the mesh covering the outlet of the ionization chamber may be made from an electrically conductive material, e.g. stainless steel, so that the mesh is shielding microwaves emitted by the ionization electrodes. In this manner, the electromagnetic radiation leaving the ionization chamber through the outlet of the ionization chamber is further reduced.

Finally, a positive direct-current voltage can be applied to the mesh to enhance plasma output and efficiency. In this manner, the electrons of the plasma within the ionization chamber are accelerated towards the mesh, so that the positively charged ions are following the electrons towards the outlet of the ionization in order to maintain an electrically neutral plasma.

Further, the mesh covering the outlet of the ionization chamber may have a mesh size of less than 5 mm or even less than 4 mm.

In accordance with exemplary embodiments of the invention, the plasma source comprises a protective cap, which is detachably attached to the outlet of the ionization chamber for preventing an over heating of the object. Therefore, the protective cap comprises at least one spacer projecting axially from the protective cap to ensure a safety distance between the outlet of the ionization chamber and the surface of the object, e.g. a wound.

In operation, the plasma source provides a flow of plasma having a comparatively low temperature, which may be below 100° C., 75° C. or even 50° C., measured on the surface of the object.

It should further be mentioned that the operating pressure within the ionization chamber is substantially equal to the ambient pressure outside the ionization chamber, so that the plasma source does not need any pressure control within the ionization chamber.

In an exemplary embodiment the outlet of the ionization chamber has a cross-section of at least 10 $cm^2$, which allows an application of the plasma to a comparatively large surface.

Further, the plasma source may be operated with a gas flow rate in the range of 1-10 l/min. However, the invention is not restricted to plasma sources operating with a gas flow rate within the aforementioned range.

In an exemplary embodiment of the invention, the plasma source further comprises a cooling means for convectively cooling the ionization chamber. The cooling means comprises at least one hollow cooling channel being disposed in the wall of the ionization chamber. During operation of the plasma source, a cooling agent, e.g. ambient air, can be pumped through the hollow cooling channels. In this manner, the temperature of the plasma is further reduced allowing in vivo plasma applications.

Further, it has to be mentioned that the plasma source may use argon to generate the plasma. However, the invention is not restricted to plasma sources using argon. For example, a mixture of argon and a few percent of nitrogen or oxygen might be used to generate the plasma, so that radicals are generated from the nitrogen/oxygen molecules.

In an exemplary embodiment the plasma source further comprises a handle on the outside of the ionization chamber for manually positioning the plasma source relative to the object, e.g. above a wound.

Finally, exemplary embodiments may include a medical device for the plasma treatment of a patient comprising the aforementioned novel plasma source. In such a medical device, the plasma torch may be mounted to a moveable arm allowing a user-defined positioning of the plasma source above the patient, wherein the moveable arm supports the plasma source, so that the plasma source need not be manually held by a therapist. The moveable arm preferably comprises several degrees of freedom of motion The embodiments and its particular features and advantages will become more apparent from the following detailed description considered with reference to the accompanying drawings.

FIGS. 1 to 4 and FIG. 8 show an exemplary embodiment of a plasma source 1, which is suitable for the in vivo sterilization of wounds.

Figure 1:
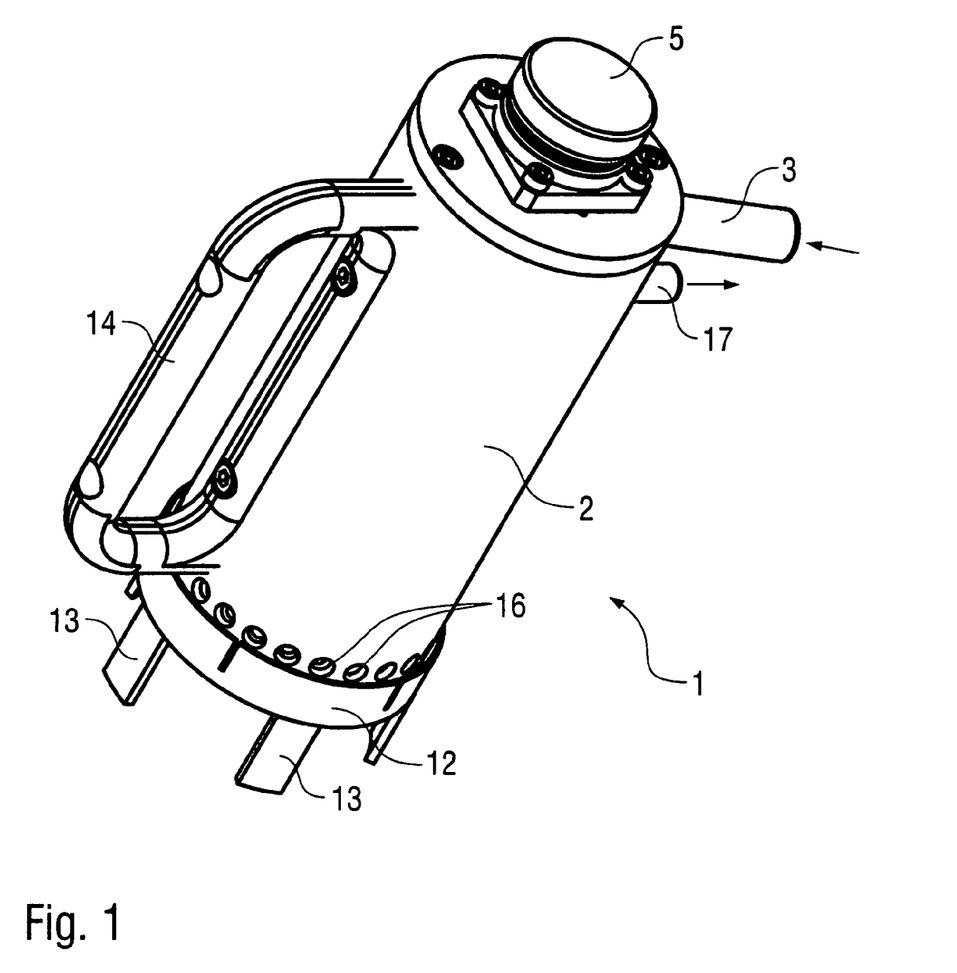
FIG. 1 is a perspective view of a plasma source according to an exemplary embodiment of the invention.
Figure 2:
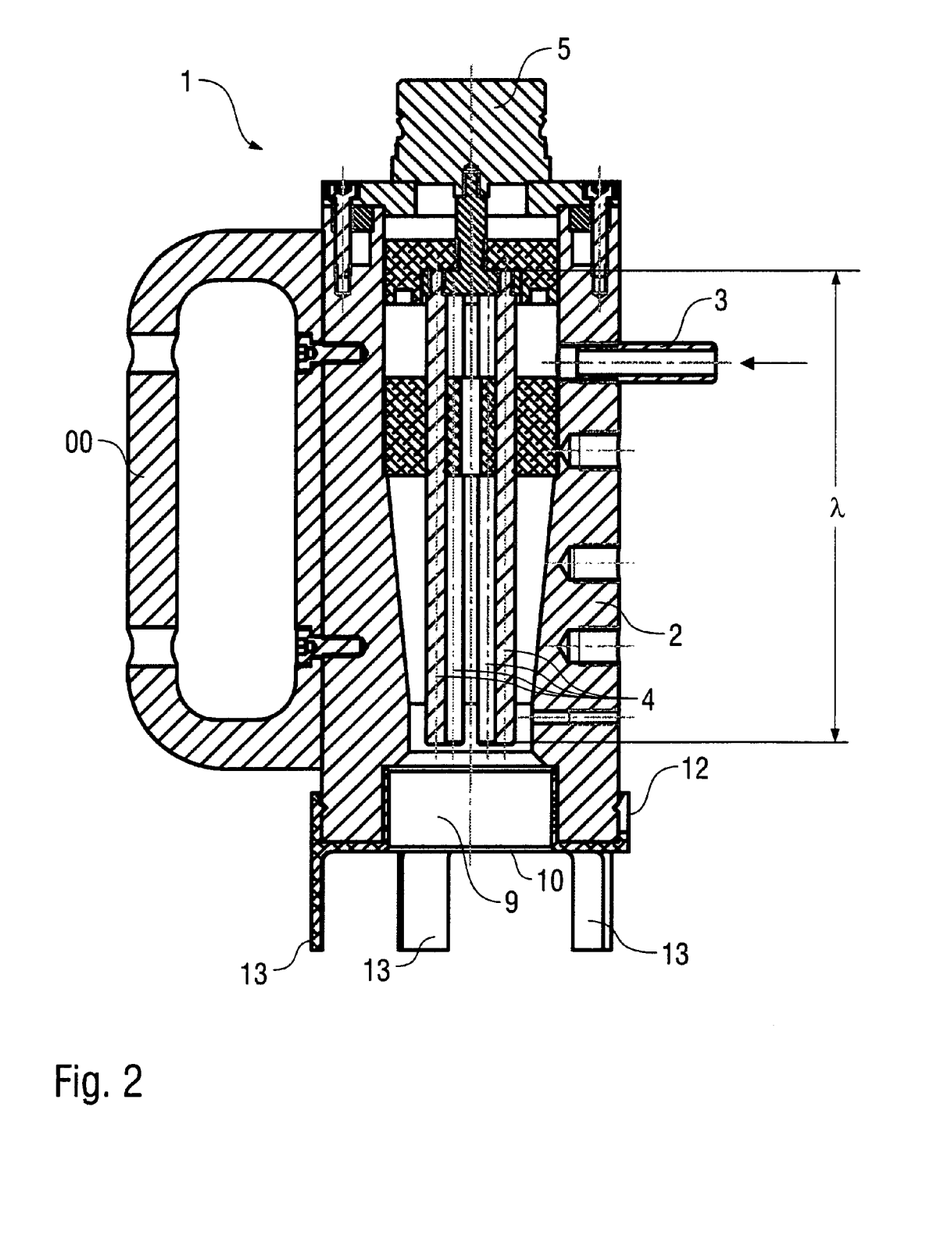
FIG. 2 is a longitudinal sectional view of the plasma source of FIG. 1.
Figure 3:
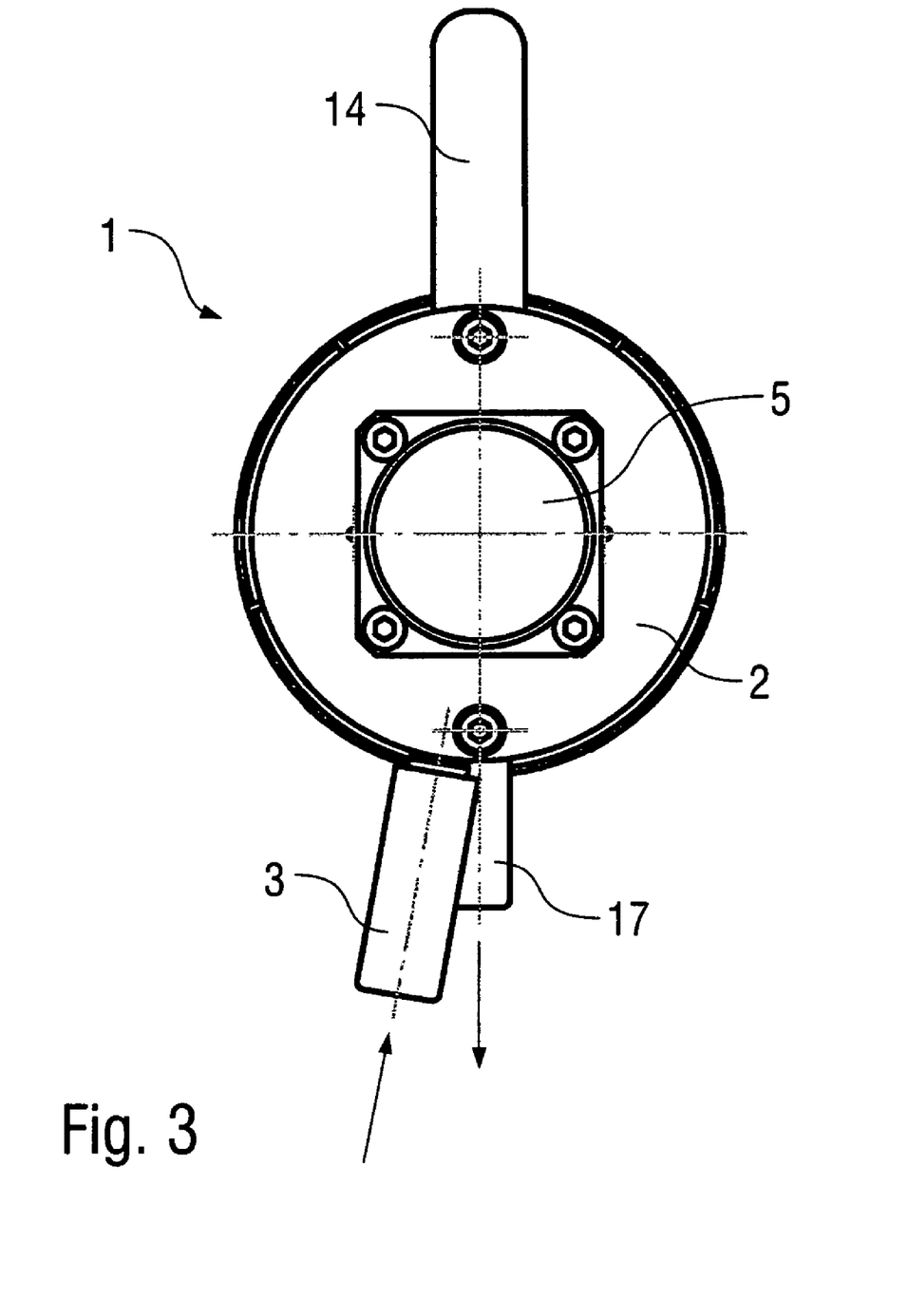
FIG. 3 is a top view of the plasma source of FIGS. 1 and 2.
Figure 4:
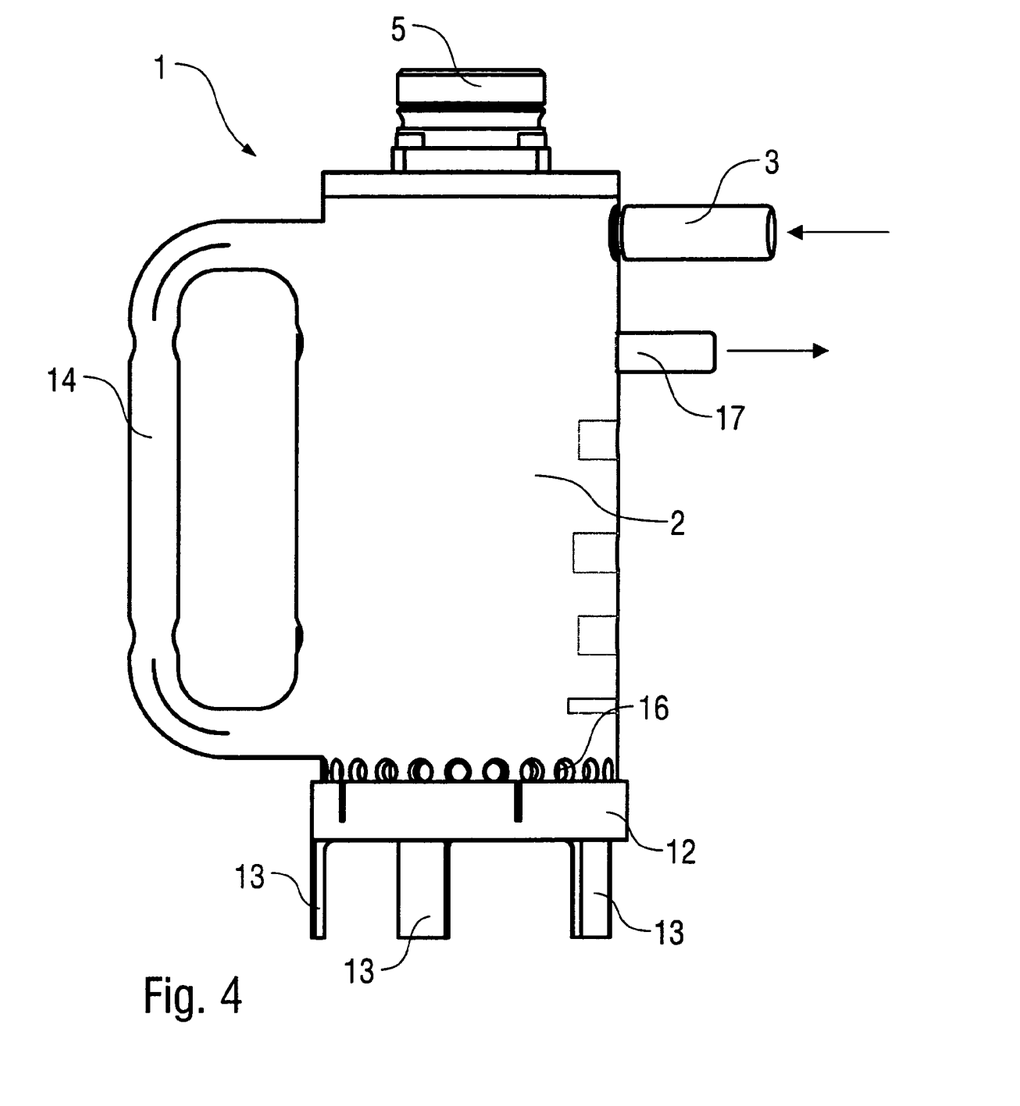
FIG. 4 is a side view of the plasma source of FIGS. 1 to 3.
Figure 7:
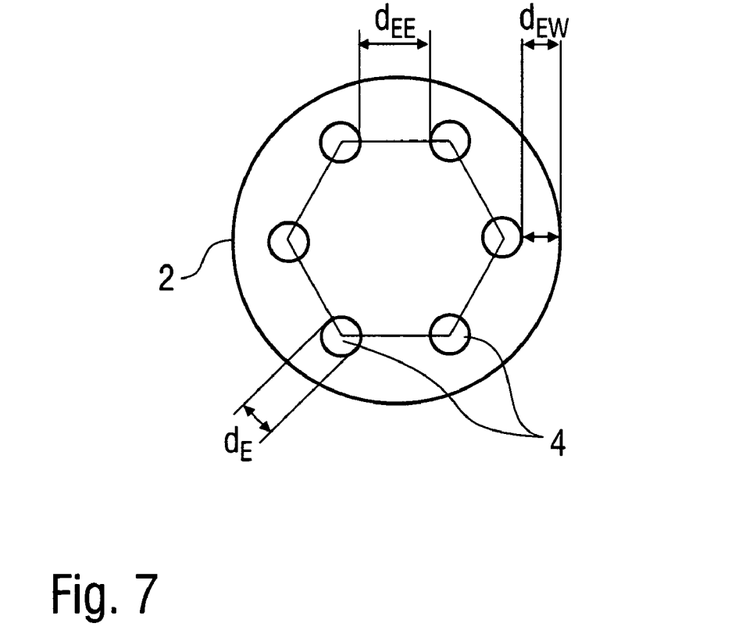
FIG. 7 is a schematic cross-sectional view of exemplary ionization electrodes in the ionization chamber of the plasma source of FIGS. 1 to 4.
Figure 8:
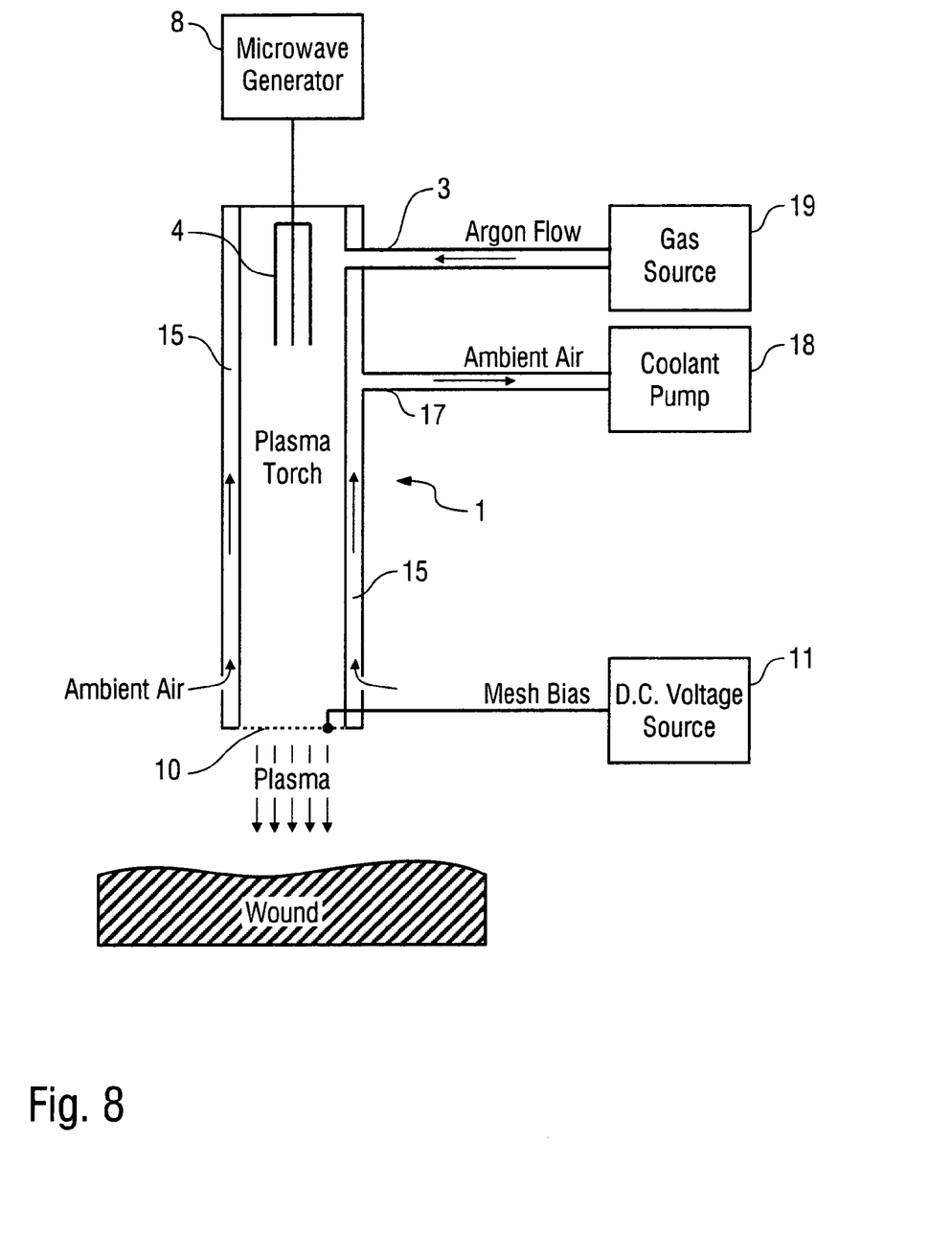
FIG. 8 is a schematic view of an exemplary plasma source of FIGS. 1 to 4 connected to a gas source, a coolant pump and a D.C. voltage source.

The plasma source 1 comprises an ionization chamber 2 having an inlet 3 for introducing an argon gas into the ionization chamber 2, where the argon gas is ionized by six ionization electrodes 4 (see FIGS. 2, 7 and 8). The ionization electrodes 4 are rod-shaped and arranged parallel to each other forming an equilateral polygon in cross-section (see FIG. 7). The ionization electrodes 4 are connected via a HF connector 5, a coaxial cable 6 and an auto tuner 7 with a conventional microwave generator 8. During operation, the microwave generator 8 generates microwaves having a specified wavelength λ, wherein the length of the ionization electrodes 4 is matched to the wavelength λ of the microwaves in such a way that the length of the ionization electrodes 4 corresponds to the wavelength λ. However, in other embodiments it is possible that the length of the ionization electrodes 4 corresponds to half the wavelength λ of the microwaves.

Further, it should be noted that there is a uniform electrode-electrode distance $d_{EE}$ between adjacent ionization electrodes 4 and also a uniform distance $d_{EW}$ between the ionization electrodes 4 and the inner wall of the ionization chamber 2. Accordingly, the ionization electrodes 4 are arranged in such a way that the ratio between the electrode-electrode distance $d_{EE}$ on the one hand and the electrode-wall-distance $d_{EW}$ is substantially 2, which results in an easy discharge trigger and a steady operation of all the ionization electrodes 4. Therefore, the plasma generation is extremely efficient, which results in a large plasma output for a low energy input, so that in vivo plasma applications are possible with low temperatures of the generated plasma and low electromagnetic irradiation.

In this embodiment, the rod-shaped ionization electrodes 4 each consist of a screw having an external thread. Therefore, the surface of the ionization electrodes 4 is serrated, which enhances the plasma generation.

Further, it should be noted that the ionization electrodes 4 are made from aluminium. An advantage of aluminium is that it does not develop a polymerized coating, which might "flake-off".

Further, the ionization chamber 2 comprises an outlet 9 (see FIG. 2) at the bottom end face of the ionization chamber 2. The outlet 9 is covered by a mesh 10 made from an electrically conductive material. The mesh 10 serves three purposes. Firstly, the mesh 10 prevents an unwanted, accidental contact with the ionization electrodes 4 within the ionization chamber 2. Secondly, the mesh 10 is shielding the microwaves generated within the ionization chamber 2, so that the electromagnetic irradiation outside the ionization chamber 2 is reduced. Finally, the mesh 10 can be electrically contacted with a direct-current voltage source 11 (see FIG. 8) to enhance plasma output and efficiency.

It should further be noted that the plasma source 1 comprises a protective cap 12, which is detachably attached to the bottom of the ionization chamber 2. The protective cap 12 comprises a central opening below the outlet 9 of the ionization chamber 2, so that the dispensing of the plasma through the outlet 9 is not interfered by the protective cap 12. The protective cap 12 comprises several spacers 13 projecting axially from the protective cap 12 to ensure a safety distance between the bottom surface of the ionization chamber 2 and the outlet 9 on the one hand and the object, e.g. a wound, on the other hand.

Further, a handle 14 is attached to the peripheral surface of the cylindrical ionization chamber 2. The handle 14 allows a manual positioning of the plasma source 1 above a wound, which will be described later.

Figure 5:
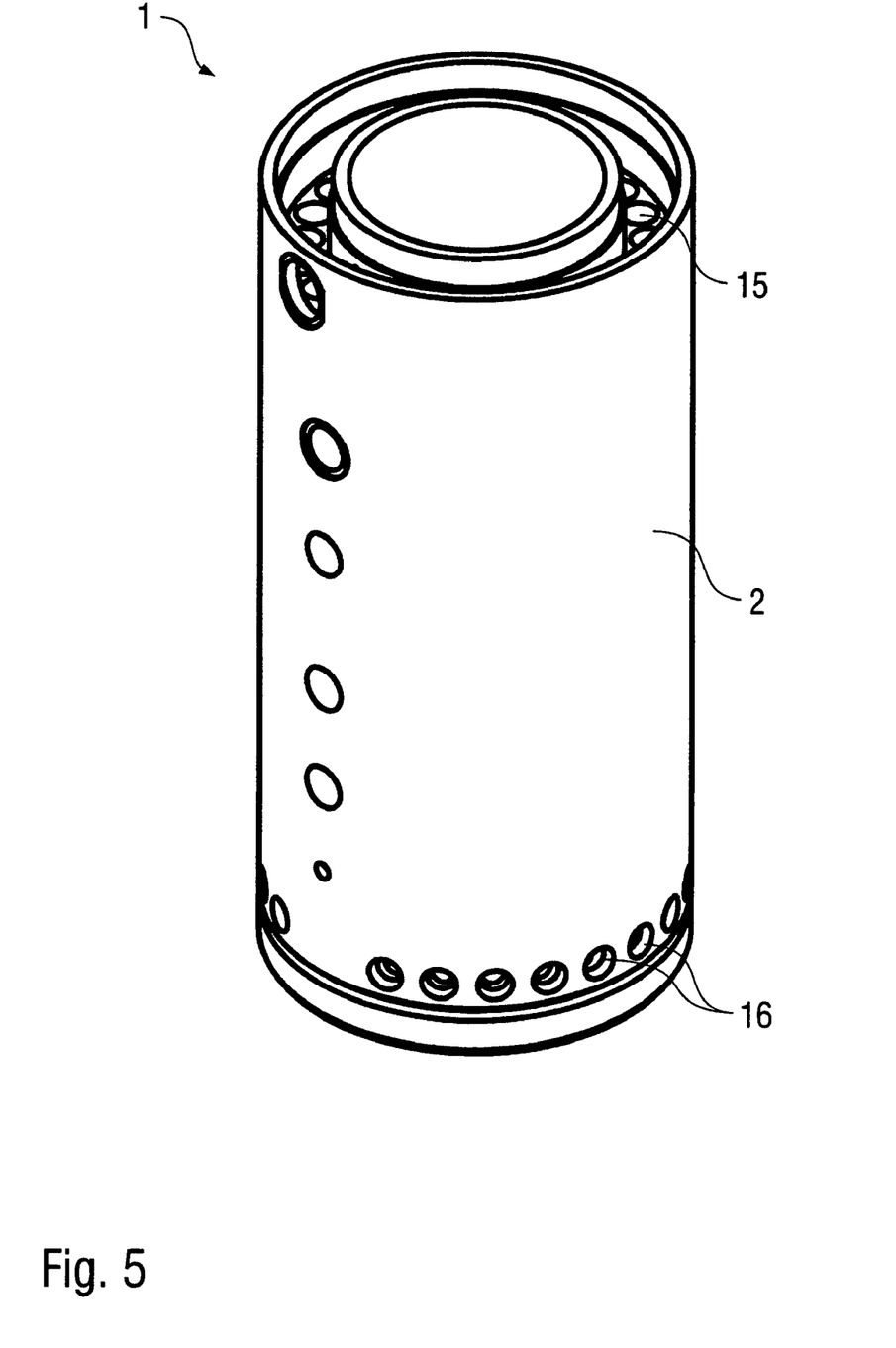
FIG. 5 is a perspective view of an exemplary ionization chamber of the plasma source of FIGS. 1 to 4.
Figure 6:
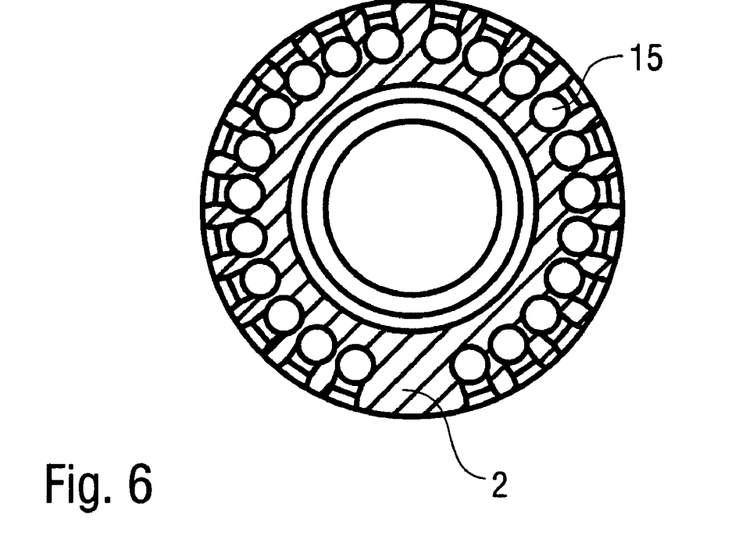
FIG. 6 is a cross-sectional view of the ionization chamber of FIG. 5.

In this embodiment, the plasma source 1 further comprises several cooling channels 15 (see FIGS. 5, 6 and 8) extending coaxially and parallel to each other within the wall of the ionization chamber 2. At the bottom of the plasma source 1, the cooling channels 15 meet in several suction holes 16, which are evenly distributed along the circumferential surface of the ionization chamber 2. At the top of the ionization chamber 2, the cooling channels 15 meet in a common outlet 17, which is connected to a coolant pump 18 (see FIG. 8). The coolant pump 18 sucks ambient air through the suction holes 16 into the cooling channels 15 thereby effectively cooling the walls of the ionization chamber 2 and also the plasma generated within the ionization chamber 2. Therefore, the cooling further reduces the temperature of the generated plasma allowing in vivo plasma applications, e.g. sterilization of wounds, treatment of bacteriological, fungicidal and viral skin disorders.

It should further be noted that the inlet 3 of the ionization chamber 2 is connected to a gas source 19 (see FIGS. 8, 9) providing an argon gas flow.

Figure 9:
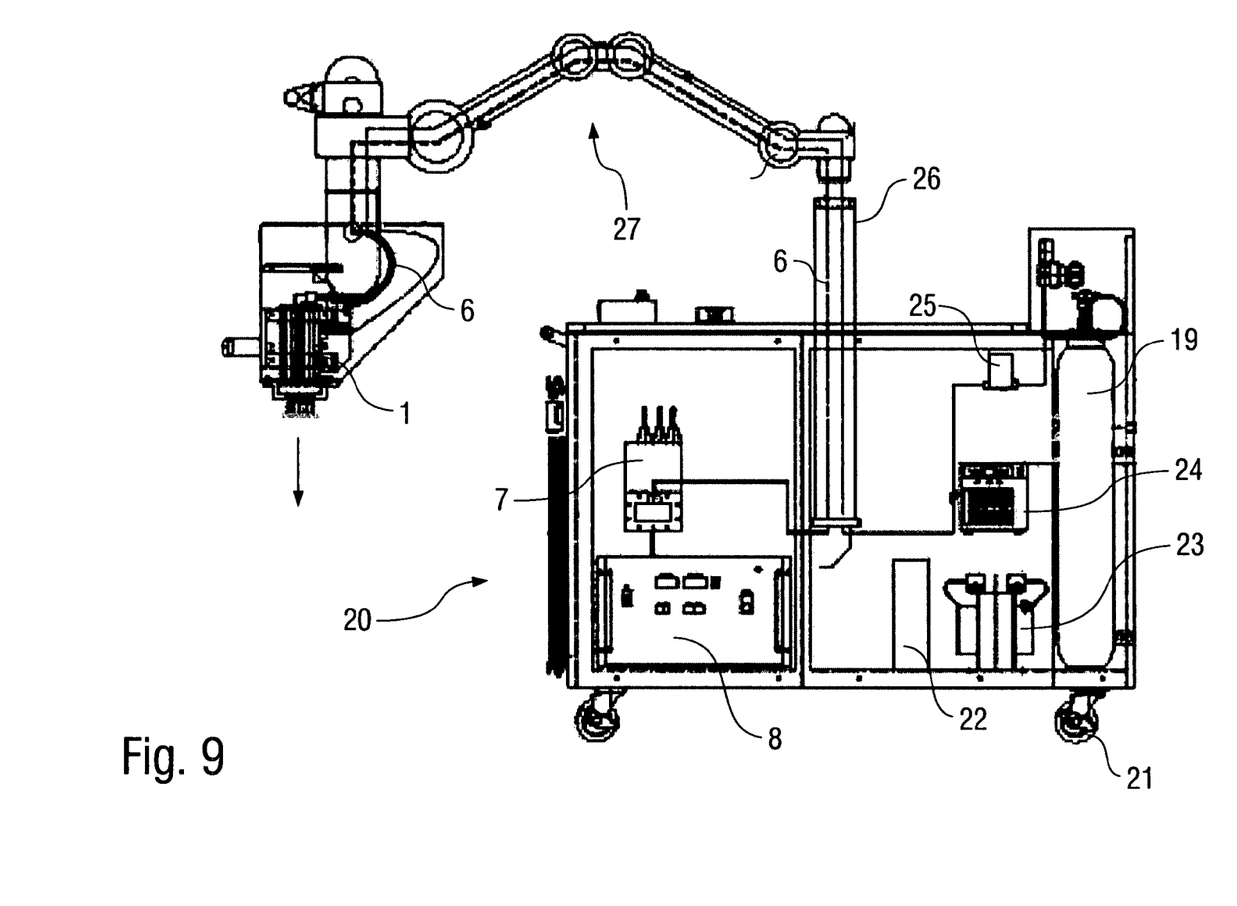
FIG. 9 is a side view of a medical device using the plasma source of FIGS. 1 to 4.

Finally, FIG. 9 shows a side view of an exemplary medical device for the plasma treatment of wounds.

The medical device comprises a carriage 20 supported on rollers 21. The carriage 20 houses the auto tuner 7, the microwave generator 8 and the gas source 19 mentioned above. Further, the carriage 20 houses an uninterruptible power supply (UPS) 22, a transformer 23, a personal computer (PC) 24 and a mass flow controller 25.

At the top of the carriage 20 there is a rotatable column 26 supporting a moveable and pivotable arm 27 having several degrees of freedom of motion. The plasma source 1 is mounted at the and of the arm 27 so that the plasma source 1 can be easily positioned above a wound by gripping the handle 14 of the plasma source 1. In the desired position the therapist can release the handle 14 of the plasma source 1, so that the arm 27 will bear the weight of the plasma source 1 during the plasma application, which may take a couple of minutes.

Although the invention has been described with reference to the particular arrangement of parts, features and the like, these are not intended to exhaust all possible arrangements of features, and indeed many other modifications and variations will be ascertainable to those of skill in the art.

The invention claimed is:

1. A plasma source comprising:
   a) an ionization chamber comprising an inlet for introducing a gas into the ionization chamber and an outlet for dispensing the ionized gas onto an object which is to be treated;
   b) wherein the outlet of the ionization chamber is covered by a mesh;
   c) several ionization electrodes being disposed within the ionization chamber for ionizing the gas;
   d) a predetermined electrode-electrode distance between the adjacent ionization electrodes;
   e) a predetermined electrode-wall distance between the ionization electrodes on the one hand and a wall of the ionization chamber on the other hand; and
   f) a predetermined ratio of the electrode-electrode distance on the one hand and the electrode-wall distance on the other hand;
   g) wherein the ratio is in a range approximately between about 1.8 and about 2.2.

2. The plasma source according to claim 1, wherein the mesh is made from an electrically conductive material, so that the mesh is shielding microwaves emitted by the ionization electrodes.

3. The plasma source according to claim 2, wherein the mesh is electrically connected to a direct-current voltage source.

4. The plasma source according to claim 1, wherein the ratio is substantially 2.

5. The plasma source according to claim 1, wherein the ratio is measured at the end of the ionization electrodes.

6. A plasma source comprising:
 a) an ionization chamber comprising an inlet for introducing a gas into the ionization chamber and an outlet for dispensing the ionized gas onto an object which is to be treated;
 b) wherein a protective cap is detachably attached to the outlet of the ionization chamber;
 c) several ionization electrodes being disposed within the ionization chamber for ionizing the gas;
 d) a predetermined electrode-electrode distance between the adjacent ionization electrodes;
 e) a predetermined electrode-wall distance between the ionization electrodes on the one hand and a wall of the ionization chamber on the other hand; and
 f) a predetermined ratio of the electrode-electrode distance on the one hand and the electrode-wall distance on the other hand;
 g) wherein the ratio is in a range approximately between about 1.8 and about 2.2.

7. The plasma source according to claim 6, wherein the protective cap comprises at least one spacer projecting axially from the protective cap to ensure a safety distance between the outlet of the ionization chamber and a surface of the object.

8. The plasma source according to claim 6, wherein the ionization electrodes are arranged substantially parallel to each other forming an equilateral polygon in cross-section.

9. The plasma source according to claim 6, wherein the ionization electrodes at least partially have a serrated surface.

10. The plasma source according to claim 9, wherein the ionization electrodes are screws having an external thread.

11. A plasma source comprising:
 a) an ionization chamber comprising an inlet for introducing a gas into the ionization chamber and an outlet for dispensing the ionized gas onto an object which is to be treated;
 b) several ionization electrodes being disposed within the ionization chamber for ionizing the gas;
 c) a cooling means for convectively cooling the ionization chamber;
 d) a predetermined electrode-electrode distance between the adjacent ionization electrodes;
 e) a predetermined electrode-wall distance between the ionization electrodes on the one hand and a wall of the ionization chamber on the other hand;
 f) a predetermined ratio of the electrode-electrode distance on the one hand and the electrode-wall distance on the other hand;
 g) wherein the ratio is in a range approximately between about 1.8 and about 2.2.

12. The plasma source according to claim 11, wherein the cooling means comprises at least one hollow cooling channel being disposed in the wall of the ionization chamber.

13. The plasma source according to claim 11, further comprising a handle at the outside of the ionization chamber for manually positioning the plasma source relative to the object.

14. The plasma source according to claim 11, wherein the ionization electrodes are electrically connected to a micro-wave generator, so that the ionization electrodes are emitting micro-waves having a predetermined wave-length.

15. The plasma source according to claim 11, wherein the wall of the ionization chamber is made from an electrically conductive material, so that the wall of the ionization chamber is shielding microwaves emitted by the ionization electrodes within the ionization chamber.

16. The plasma source according to claim 11, wherein there is an operating pressure within the ionization chamber, which is substantially equal to the ambient pressure outside the ionization chamber.

17. A medical device for a plasma treatment of a patient, comprising a plasma source comprising:
 a) an ionization chamber comprising an inlet for introducing a gas into the ionization chamber and an outlet for dispensing the ionized gas onto an object which is to be treated;
 b) several ionization electrodes being disposed within the ionization chamber for ionizing the gas;
 c) a predetermined electrode-electrode distance between the adjacent ionization electrodes;
 d) a predetermined electrode-wall distance between the ionization electrodes on the one hand and a wall of the ionization chamber on the other hand; and
 e) a predetermined ratio of the electrode-electrode distance on the one hand and the electrode-wall distance on the other hand;
 f) wherein the ratio is in a range approximately between about 1.8 and about 2.2.

18. The medical device according to claim 17, wherein the plasma source is mounted to a movable arm allowing a user-defined positioning of the plasma source above the patient, wherein the movable arm supports the plasma source, so that the plasma source need not be manually held by a therapist.

* * * * *